United States Patent
Linares (10) Patent No.: US 11,951,015 B2
(45) Date of Patent: Apr. 9, 2024

(54) EXPANDABLE WORM SCREW JACK FOR INSTALLATION BETWEEN UPPER AND LOWER SUCCEEDING ARTICULAR PROCESSES

(71) Applicant: Linares Spinal Devices, LLC, Auburn Hills, MI (US)

(72) Inventor: Miguel A. Linares, Bloomfield Hills, MI (US)

(73) Assignee: Linares Spinal Devices, LLC, Auburn Hills, MI (US)

( * ) Notice: Subject to any disclaimer, the term of this patent is extended or adjusted under 35 U.S.C. 154(b) by 0 days.

(21) Appl. No.: 18/081,008

(22) Filed: Dec. 14, 2022

(65) Prior Publication Data

US 2023/0233333 A1    Jul. 27, 2023

Related U.S. Application Data

(60) Provisional application No. 63/302,182, filed on Jan. 24, 2022.

(51) Int. Cl.
*A61F 2/44*    (2006.01)
*A61F 2/30*    (2006.01)

(52) U.S. Cl.
CPC .... *A61F 2/4405* (2013.01); *A61F 2002/3055* (2013.01); *A61F 2002/30579* (2013.01)

(58) Field of Classification Search
CPC ............ A61B 17/7062; A61B 17/7065; A61B 17/7067; A61B 17/7068
See application file for complete search history.

(56) References Cited

U.S. PATENT DOCUMENTS

| | | | |
|---|---|---|---|
| 8,545,563 B2 | 10/2013 | Bun et al. | |
| 8,585,738 B2* | 11/2013 | Linares | A61B 17/8605 |
| | | | 606/248 |
| 8,623,056 B2 | 1/2014 | Linares | |
| 9,023,108 B2* | 5/2015 | Hansell | A61F 2/44 |
| | | | 623/17.15 |
| 9,474,626 B2* | 10/2016 | Jimenez | A61F 2/4611 |
| 10,238,383 B2* | 3/2019 | Moskowitz | A61B 17/0682 |
| 10,952,723 B2 | 3/2021 | Moskowitz et al. | |
| 11,432,937 B1 | 9/2022 | Linares | |
| 11,491,028 B2* | 11/2022 | Carnes | A61F 2/447 |
| 2006/0136062 A1* | 6/2006 | DiNello | A61F 2/4425 |
| | | | 623/18.12 |
| 2011/0251692 A1* | 10/2011 | McLaughlin | A61F 2/4455 |
| | | | 623/17.16 |
| 2020/0030116 A1 | 1/2020 | Jimenez et al. | |

(Continued)

*Primary Examiner* — Ellen C Hammond
*Assistant Examiner* — Holly Joanna Lane
(74) *Attorney, Agent, or Firm* — Dinsmore & Shohl LLP (57) ABSTRACT

A spinal jack adapted for installation between first and second vertebral processes and includes a three dimensional and arcuate ergonomic main body constructed from a first and second portions, from which is displaceable an upper body between each of retracted and expanded positions. Each of the jack halves includes gripping portions adapted for engaging the vertebral processes. A worm gear mechanism includes a central horizontally arrayed and rotatable worm gear supported within the main body and accessible through an inlet aperture. A tool bit is engageable with a bit receiving location of the worm gear which is accessible through the inlet aperture.

18 Claims, 6 Drawing Sheets

(56) References Cited

U.S. PATENT DOCUMENTS

2020/0337852 A1* 10/2020 McLuen ............... A61F 2/4657
2021/0052307 A1   2/2021 Soo et al.
2022/0323235 A1  10/2022 Peyman et al.

* cited by examiner

EXPANDABLE WORM SCREW JACK FOR INSTALLATION BETWEEN UPPER AND LOWER SUCCEEDING ARTICULAR PROCESSES

CROSS REFERENCE TO RELATED APPLICATIONS

The present application claims the priority of U.S. Ser. No. 63/302,182 filed Jan. 24, 2022.

FIELD OF THE INVENTION

The present invention relates generally to spinal jacks for providing inter-vertebral support. More specifically, the present invention teaches an adjustable spinal jack for installation between superior articular processes of upper and lower succeeding vertebrae.

BACKGROUND OF THE INVENTION

Spinal jacks designs are known in the prior art for providing adjusted and secure positioning support between succeeding spinal vertebra. Examples of these are depicted in each of Linares U.S. Pat. No. 8,623,056 and Linares U.S. Pat. No. 8,585,738.

SUMMARY OF THE PRESENT INVENTION

The present application discloses a spinal jack adapted for installation between first and second vertebral processes and includes a three dimensional and arcuate ergonomic main body constructed from a first and second subset portions, from which is displaceable an upper body between each of retracted and expanded positions. Each of the jack halves includes gripping portions adapted for engaging the vertebral processes. A worm gear mechanism expands or retracting the jack halves in order to establish a corrected adjusted orientation between the processes.

The worm gear mechanism further includes a central horizontally arrayed and rotatable worm gear supported within the main body accessible through an inlet aperture. A tool bit is engageable with a bit receiving location of the worm gear, accessible through the inlet aperture.

A spiral array of teeth extends along a generally horizontal length of the worm gear which mesh with crosswise bevel arranged and annular gear teeth arranged upon each of a pair of outer gears arranged upon opposite sides of the worm gear.

The upper body further includes a pair of downwardly extending stems anchored at upper ends to lateral outer locations of the upper body. The stems extend downwardly and respectively seating within and through elongated interior channels or passageways defined in an upper located of the main body subset portions. The upper subset body portion includes lateral superstructures with additional interior channels in alignment with the interior channels in the upper body.

Bottom extending portions of the stems each further include additional worm gear configurations, which rotatably engage inner spiraling threads configured in the outer gears. The body and inter-expandable jack halves further include any medical grade metal or plastic.

The gripping portions each further include spaced apart sides and an interconnected recessed end defining a pocket adapted to receive the vertebral process therebetween. The pockets each further include textured surfaces for providing additional gripping of the vertebral processes.

Each of the first and second subset portions of said main body further include an opposing base within which is configured a recessed cavity for receiving the central worm gear and outer bevel gears. Additional cavities are also configured into the main body for seating the displaceable stems.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

With reference to the attached illustrations, the present invention discloses an adjustable spinal jack for installation between superior articular processes of upper and lower succeeding vertebrae. A general representation of a selected jack is depicted generally at 10 in a retracted position in FIG. 1, and is further shown in each of succeeding FIGS. 2-3 positioned between upper 2 and lower 4 successive superior articular processes corresponding to upper and lower vertebrae.

The present invention provides an expandable spinal jack which overcomes a number of the disadvantages of the prior art and provides an effective solution for stabilizing and fixing in position a given orientation established between the succeeding vertebrae. As will be further described, the spinal jack permits adjustment, at any future time following initial surgical implantation, in a minimally invasive fashion and in order to re-adjust the spatial positioning established between the upper and lower separable halves or sections, such as in order to compensate and correct for future/downstream vertebral complications following the initial implantation of the spinal jack.

Figure 1:
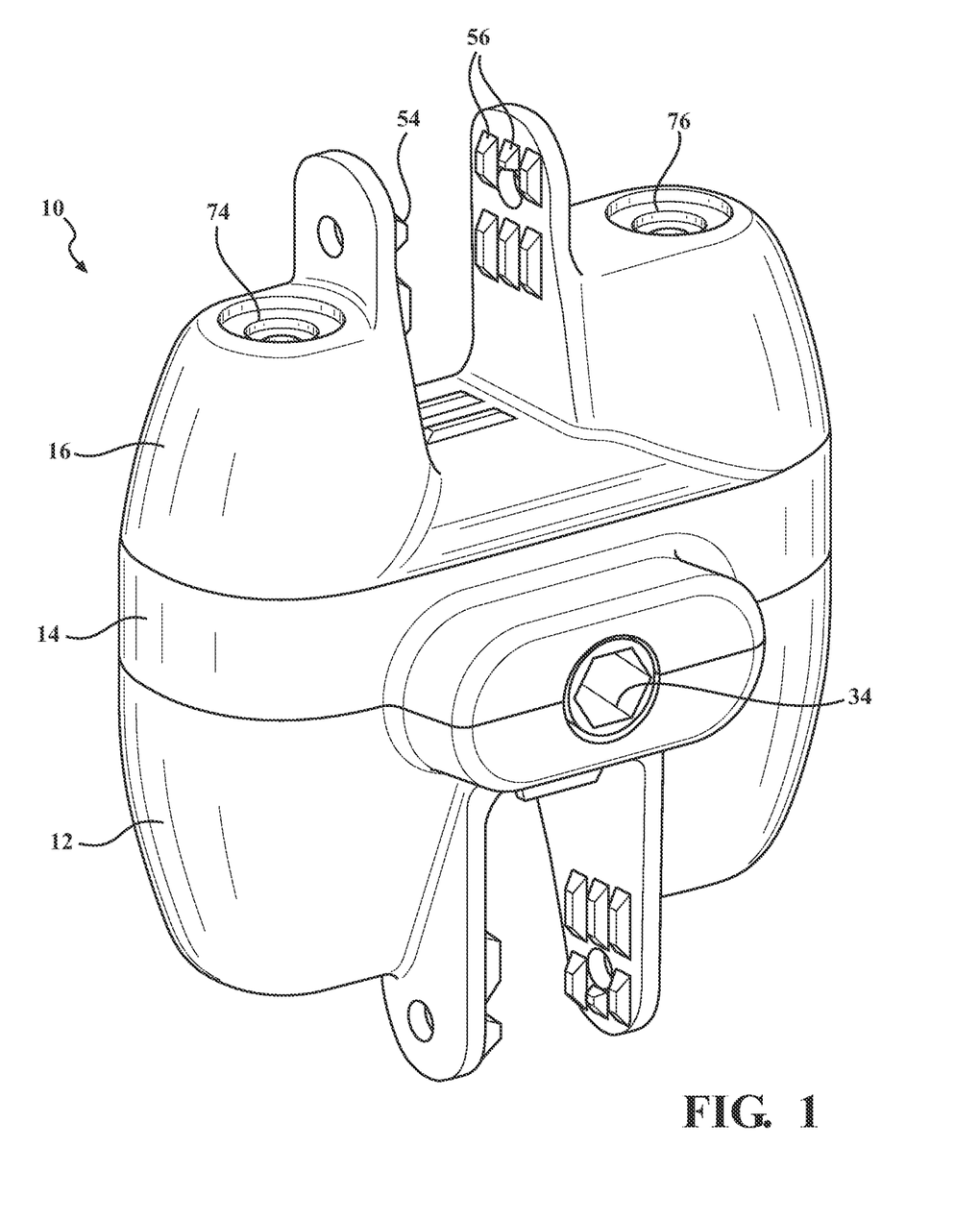
FIG. 1 is a perspective view of a spinal worm screw jack according to one non-limiting variant and having first and second spinal jack halves shown in a retracted position prior to being installed between succeeding superior articular processes associated with upper and lower consecutive spinal vertebra.
Figure 3:
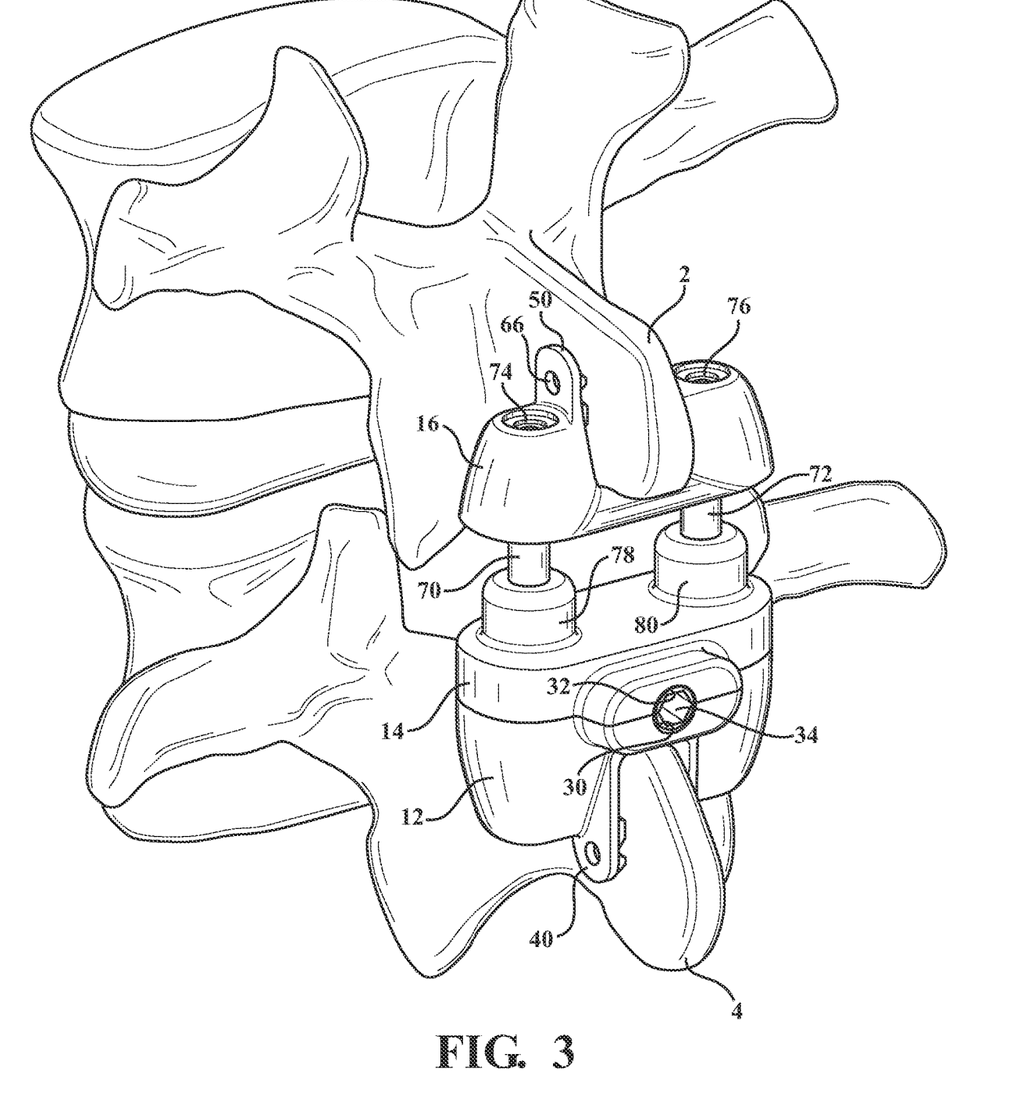
FIG. 3 is a succeeding view to FIG. 2 and depicting the spinal jack in an expanded position for properly orienting the vertebrae.

Proceeding to FIG. 1, an environmental illustration is generally shown of the spinal jack 10 substantially as shown in FIG. 1 in a retracted position. In combination with the expanded position of FIG. 3, the spinal jack includes a three dimensional and arcuate ergonomic main body, this constructed from first 12 and second 14 subset body portions, from which is displaceable an upper body 16 (as best shown in FIG. 3). The main body 12/14 and upper displace-able body 16 are each constructed of a suitable sanitary medical grade material not limited to any of a metal or plastic composition.

Each of the main body subset portions 12 and 14 are arranged in a mirrored opposing and abutting end face orientation. An interior recessed cavity is defined between the base subset portions 12 and 14 and, as best shown, includes aligning locations formed within each opposing base surface.

Figure 4:
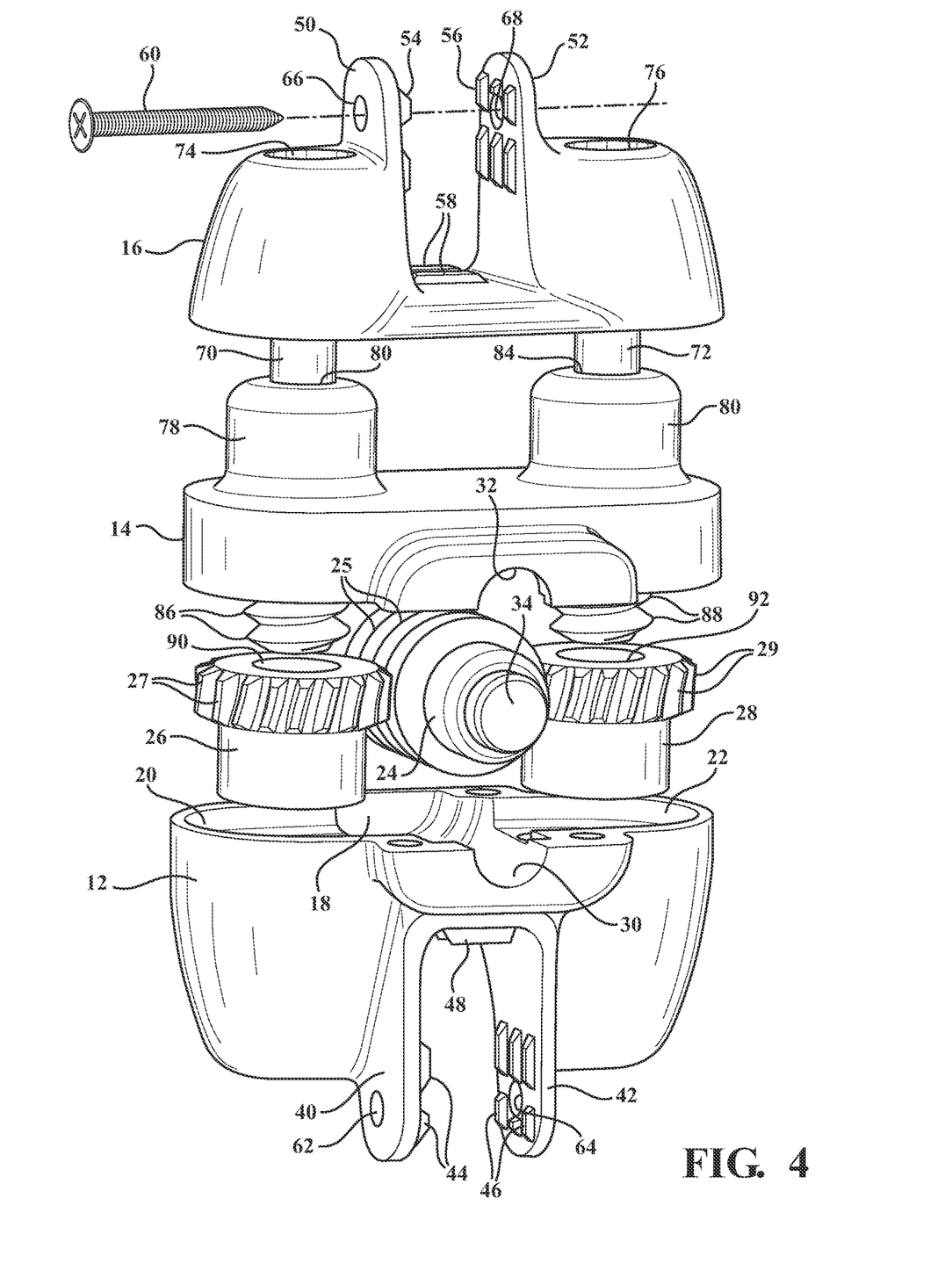
FIG. 4 is an exploded view of the spinal jack assembly and depicting the interior worm screw and gearing for separating the upper and lower halves.

As best depicted in FIG. 4, a central cavity location 18 and adjoining lateral or peripheral cavity locations 20 and 22 are associated with the subset body portion 12 (a similar opposing configuration being formed in the hidden underside of the upper located subset body portion 14), these collectively seating a worm gear mechanism including a central worm gear 24 and a pair of inter-engaging, outer beveled and actuated gears 26/28 in a side-by-side configuration. As shown in FIG. 4, the worm gear 24 includes a spiral array of teeth 25 extending along its generally horizontal length which mesh with crosswise bevel arranged and annular gear teeth, shown at 27 arranged upon outer gear 26, as well as further shown at 29 arranged upon the other outer gear 28.

An inlet aperture to the central worm gear 24 is provided by subset rim portions 30 and 32, these being defined in aligning fashion between the opposing end faces of the subset body portions 12/14. In this fashion, a tool bit or the like (not shown) can be inserted within the inlet aperture into engagement with a central bit receiving location 34 for actuating the worm gear 24 and meshing outer beveled gears 26/28. The present invention contemplates any bit configuration for rotating the central worm gear 24, such including without limitation a hex key profile as depicted.

Each of the subset body portions 12/14 also depict inwardly contoured or recessed channels for receiving the superior articular processes 2 and 4. A first lower channel is configured in the lower positioned the subset body portion 12 and is defined by a pair spaced apart extending sides 40/42, each further exhibiting opposing side surface gripping locations 44/46, with a further middle gripping location 48 defining an inside base surface interconnecting the side locations for configuring a first superior articular process receiving pocket.

As shown, the upper body 16 includes an upper recessed channel defined by a further pair of spaced apart sides 50/52, each further exhibiting opposing side surface gripping locations 54/56 and a further inside located middle gripping location 58 interconnecting the sides 50/52 for configuring a second superior articular process receiving pocket. The spaced apart pockets defining each of the opposite extending gripping portions are adapted to seat the upper 2 and lower 4 consecutive superior articular processes, with the gripping portions configured upon the inner "U" shaped surface profile of each pocket exhibited by any type of textured or ribbed profile, the purpose of which is to provide additional resistive engagement against the opposing facet surfaces of the processes 2 and 4.

Any type of screw fastener (such as shown at 60 in FIG. 4) is employed with each gripping portion and which, upon positioning the gripping portions and drilling through the processes 2 and 4 (in alignment with aligning pairs of apertures 62/64 and 66/68 formed through the spaced apart pairs of sides 40/42 and 50/52), provides for anchoring the lower and upper jack halves to the respective vertebrae. Alternatively, the gripping portions defining each pocket can be provided without aligning apertures (see related variant of FIG. 1), and which can be crimped into engagement with the vertebral processes 2 and 4, such as without the use of separate screws.

As best shown in FIGS. 3-4, the upper body 16 includes a pair of elongated stems 70 and 72 which are anchored at upper ends to lateral locations (shown by interior channels 74 and 76) in the upper body 16. The stems 70/72 extend downwardly and respectively seat within and through elongated interior channels or passageways defined in the upper subset portion 14 of the main body (see lateral superstructures 78 and 80 of the upper subassembly portion 14 with similar interior channels 82/84 in alignment with those at 74/76 in the upper body 16 for seating the stems 70/72).

Figure 2:
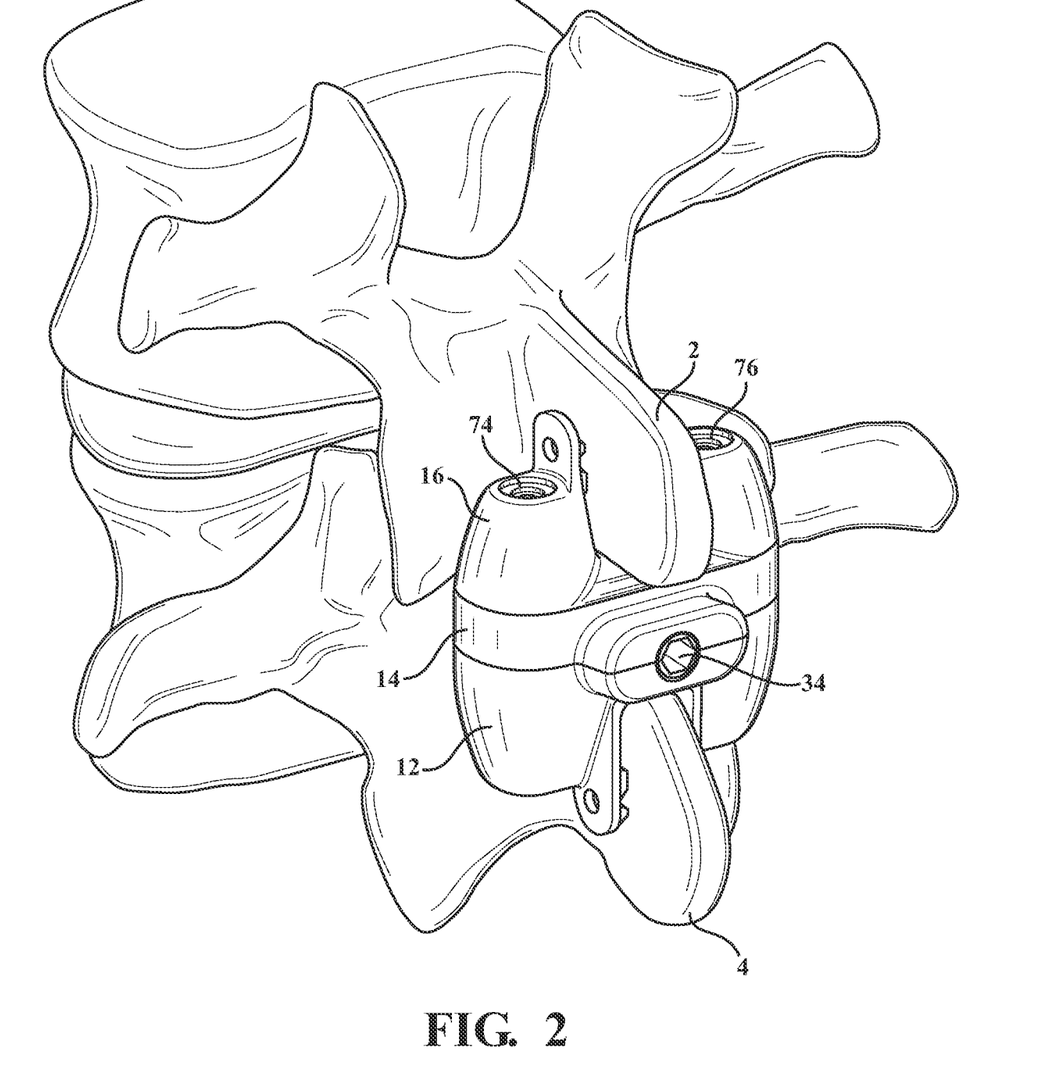
FIG. 2 is an environmental illustration of a spinal jack of FIG. 1 depicted in a retracted position installed between succeeding superior articular processes associated with upper and lower consecutive spinal vertebrae.

As again shown in FIG. 4, bottom extending portions of each stem 70/72 further exhibit additional worm gear configurations (see at 86 and 88) which rotatably engage inner spiraling threads 90 and 92 configured in the outer actuated gears 26/28. In this fashion, and upon pre-positioning and initial attachment of the spinal jack 10 between the succeeding superior articular processes as best shown in FIG. 2, the tool bit is inserted through the collectively defined aperture (collectively at 30/32) and into the (hex) bit receiving recess 34 of the central worm gear 24 and further, upon being rotated in a selected rotational direction, results in the outer bevel supported gears 26/28 being rotated. Simultaneously, the inner spiral threads 90/92 of the outer gears 26/28 in turn actuate the inter-engaged worm gear ends 86/88 of the stems 70/72 in order to elevate the stems and upper end supported spinal jack body 16.

In this manner, the stems 70/72 are elevated along with the upper supported and process engaging body 16 relative to the assembled subset portions 12/14 of the lower main body. As again best shown in FIG. 4, additional recesses can be defined in the lower body portions 12/14 corresponding to seating locations 20/22 for seating extending displaceable ends of the stems 70/72 in a manner allowing a desired degree of travel of the worm gear ends 86/88 relative to the outer gears 26/28 for bi-directional adjustment of the upper spinal jack half 16 relative to the inter-assembled lower spinal jack half 12/14. Although not shown, it is envisioned and understood that additional spinal braces and the like can be provided (not shown) which can be installed against the later processes of each vertebrae and in order to provide additional vertebral support depending upon the nature of the spinal injury being addressed.

Figure 5:
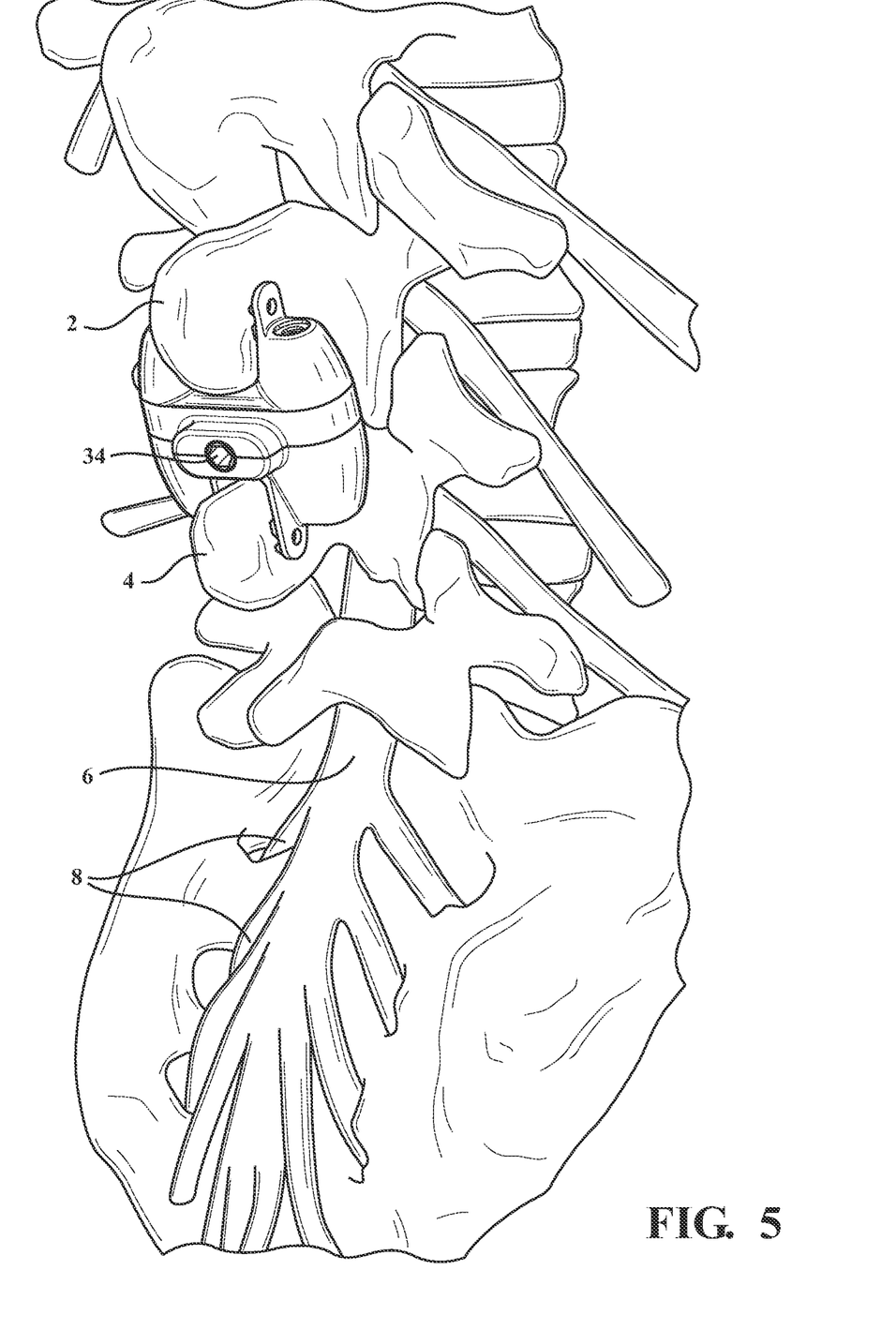
FIG. 5 corresponds to FIG. 2 and provides an environmental depiction of the spinal jack initially installed in a retracted position between succeeding vertebrae shown along with the vertebral column and spinal cord with branching locations.
Figure 6:
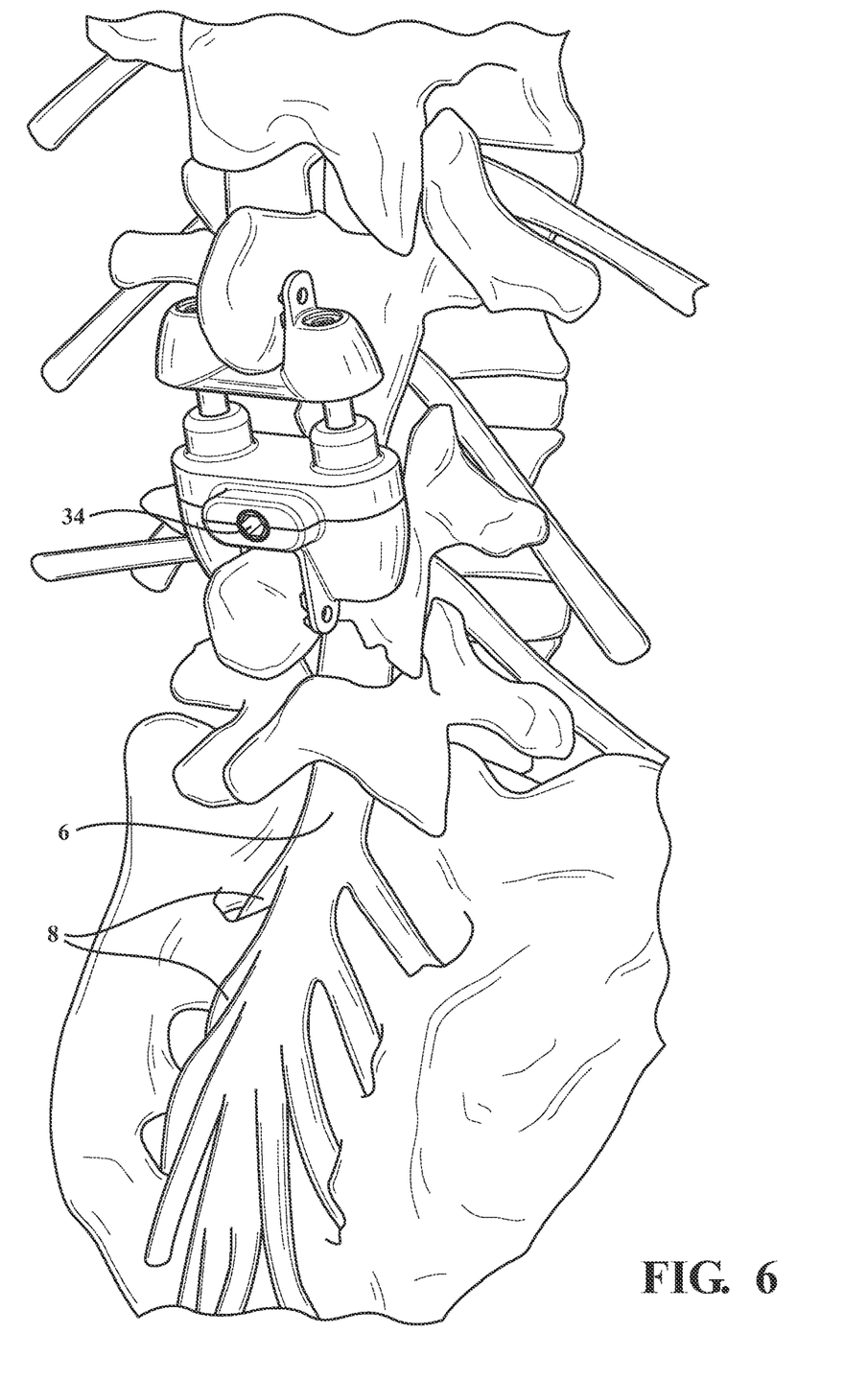
FIG. 6 is similar to FIG. 5 and corresponds to FIG. 3, providing an environmental depiction of the spinal jack initially expanded to a final adjusted position between the succeeding vertebrae shown along with the vertebral column and spinal cord with branching locations.

FIG. 5 corresponds to FIG. 2 and provides an environmental depiction of the spinal jack 10, initially installed in a retracted position between succeeding vertebrae, and shown along with the vertebral column and associated spinal cord 6 with branching locations 8. Finally, FIG. 6 is similar to FIG. 5 and corresponds to FIG. 3, providing an environmental depiction of the spinal jack initially expanded to a final adjusted position between the succeeding vertebrae shown along with the vertebral column and spinal cord with branching locations.

Having described my invention, other and additional preferred embodiments will become apparent to those skilled in the art to which it pertains, and without deviating from the scope of the appended claims. The detailed description and drawings are further understood to be supportive of the disclosure, the scope of which being defined by the claims. While some of the best modes and other embodiments for carrying out the claimed teachings have been described in detail, various alternative designs and embodiments exist for practicing the disclosure defined in the appended claims.

The foregoing disclosure is further understood as not intended to limit the present disclosure to the precise forms or particular fields of use disclosed. As such, it is contemplated that various alternate embodiments and/or modifications to the present disclosure, whether explicitly described or implied herein, are possible in light of the disclosure. Having thus described embodiments of the present disclosure, a person of ordinary skill in the art will recognize that changes may be made in form and detail without departing from the scope of the present disclosure. Thus, the present disclosure is limited only by the claims.

In the foregoing specification, the disclosure has been described with reference to specific embodiments. However, as one skilled in the art will appreciate, various embodiments disclosed herein can be modified or otherwise implemented in various other ways without departing from the spirit and scope of the disclosure. Accordingly, this description is to be considered as illustrative and is for the purpose of teaching those skilled in the art the manner of making and using various embodiments of the disclosure. It is to be understood that the forms of disclosure herein shown and described are to be taken as representative embodiments. Equivalent elements, materials, processes or steps may be substituted for those representatively illustrated and described herein. Moreover, certain features of the disclosure may be utilized independently of the use of other features, all as would be apparent to one skilled in the art after having the benefit of this description of the disclosure. Expressions such as "including", "comprising", "incorporating", "consisting of", "have", "is" used to describe and claim the present disclosure are intended to be construed in a non-exclusive manner, namely allowing for items, components or elements not explicitly described also to be present. Reference to the singular is also to be construed to relate to the plural.

Further, various embodiments disclosed herein are to be taken in the illustrative and explanatory sense, and should in no way be construed as limiting of the present disclosure. All joinder references (e.g., attached, affixed, coupled, connected, and the like) are only used to aid the reader's understanding of the present disclosure, and may not create limitations, particularly as to the position, orientation, or use of the systems and/or methods disclosed herein. Therefore, joinder references, if any, are to be construed broadly. Moreover, such joinder references do not necessarily infer that two elements are directly connected to each other.

Additionally, all numerical terms, such as, but not limited to, "first", "second", "third", "primary", "secondary", "main" or any other ordinary and/or numerical terms, should also be taken only as identifiers, to assist the reader's understanding of the various elements, embodiments, variations and/or modifications of the present disclosure, and may not create any limitations, particularly as to the order, or preference, of any element, embodiment, variation and/or modification relative to, or over, another element, embodiment, variation and/or modification.

It will also be appreciated that one or more of the elements depicted in the drawings/figures can also be implemented in a more separated or integrated manner, or even removed or rendered as inoperable in certain cases, as is useful in accordance with a particular application. Additionally, any signal hatches in the drawings/figures should be considered only as exemplary, and not limiting, unless otherwise specifically specified.

The invention claimed is:

1. A spinal jack adapted for installation between first and second vertebral processes, comprising:
    a main body constructed from first and second subset body portions;
    an upper body supported upon said main body between retracted and expanded positions;
    said upper body further including a pair of downwardly extending stems seating within said main body;
    each of said bodies further including gripping portions adapted for engaging the vertebral processes;
    a worm gear mechanism having a rotatable worm gear supported within said main body and accessible through an inlet aperture for rotating a pair of outer gears which in turn interact with said stems for expanding or retracting said upper body relative to said main body in order to establish a corrected adjusted orientation between the processes; and
    each of said first and second subset portions of said main body further including an opposing base within which is configured a recessed cavity for receiving said worm gear and said outer gears, said recessed cavity further including a central cavity location and adjoining peripheral cavity locations defined in said first subset body portion, said inlet aperture further including aligning subset rim portions defined in said first and second subset body portions.

2. The spinal jack of claim 1, said rotatable worm gear further comprising a spiral array of teeth extending along its generally horizontal length, wherein said spiral array of teeth from a crosswise bevel with annular gear teeth arranged upon each of said pair of outer gears which are arranged upon opposite sides of said worm gear.

3. The spinal jack of claim 2, further comprising said downwardly extending stems anchored at upper ends to lateral locations of said upper body, said stems seating within and through elongated interior channels defined in said second subset body portion.

4. The spinal jack of claim 3, said second subset body portion of said main body further comprising lateral superstructures with additional interior channels in alignment with said interior channels in said upper body.

5. The spinal jack of claim 3, further comprising bottom extending portions of said stems each further comprising additional worm gear configurations which rotatably engage inner spiraling threads configured in said outer gears.

6. The spinal jack of claim 1, further comprising a tool bit engageable with a bit receiving location of said worm gear accessible through said inlet aperture.

7. The spinal jack of claim 1, said body and inter-expandable jack halves further comprising any medical grade metal or plastic.

8. The spinal jack of claim 1, said gripping portions each further comprising spaced apart sides and an interconnected recessed end defining a pocket adapted to receive the vertebral process therebetween.

9. The spinal jack of claim 8, said pockets each further including textured surfaces for providing additional gripping of the vertebral processes.

10. The spinal jack of claim 1, further comprising cavities configured into said subset portions of said main body for seating said displaceable stems.

11. A spinal jack adapted for installation between first and second vertebral processes, comprising:

a three dimensional and arcuate ergonomic main body constructed from first and second subset body portions;

an upper body supported upon said main body between retracted and expanded positions;

said upper body further including a pair of downwardly extending stems seating within said main body;

each of said bodies further including gripping portions adapted for engaging the vertebral processes;

a worm gear mechanism having a rotatable worm gear supported within said main body and accessible through an inlet aperture provided for expanding or retracting said upper body relative to said main body in order to establish a corrected adjusted orientation between the processes, said rotatable worm gear including a spiral array of teeth extending along its generally horizontal length, wherein said spiral array of teeth form a crosswise bevel with annular gear teeth arranged upon each of a pair of outer gears arranged upon opposite sides;

each of said first and second subset portions of said main body further including an opposing base within which is configured a recessed cavity for receiving said worm gear and said outer gears, said recessed cavity further including a central cavity location and adjoining peripheral cavity locations defined in said first subset body portion, said inlet aperture further including aligning subset rim portions defined in said first and second subset body portions; and bottom extending portions of said stems each further comprising additional worm gear configurations which rotatably engage inner spiraling threads configured in said outer gears.

12. The spinal jack of claim 11, further comprising said downwardly extending stems anchored at upper ends to lateral locations of said upper body, said stems seating within and through elongated interior channels defined in said second subset body portion.

13. The spinal jack of claim 11, said second subset body portion of said main body further comprising lateral superstructures with additional interior channels in alignment with said interior channels in said upper body.

14. The spinal jack of claim 11, further comprising a tool bit engageable with a bit receiving location of said worm gear accessible through said inlet aperture.

15. The spinal jack of claim 11, said body and interexpandable jack halves further comprising any medical grade metal or plastic.

16. The spinal jack of claim 11, said gripping portions each further comprising spaced apart sides and an interconnected recessed end defining a pocket adapted to receive the vertebral process therebetween.

17. The spinal jack of claim 16, said pockets each further including textured surfaces for providing additional gripping of the vertebral processes.

18. The spinal jack of claim 11, further comprising cavities configured into said subset portions of said main body for seating said displaceable stems.

* * * * *